(12) United States Patent
Angelini et al.

(10) Patent No.: US 12,729,358 B2
(45) Date of Patent: Sep. 8, 2026

(54) CAPILLARY-DRIVEN PERFUSION SYSTEMS AND METHODS OF USE

(71) Applicant: University of Florida Research Foundation, Inc., Gainesville, FL (US)

(72) Inventors: Thomas E. Angelini, Gainesville, FL (US); Obiora Azie, Gainesville, FL (US); Jon P. Dobson, Gainesville, FL (US); Peter S. McFetridge, Gainesville, FL (US); Cameron D. Morley, Gainesville, FL (US); Malisa Sarntinoranont, Gainesville, FL (US)

(73) Assignee: University of Florida Research Foundation, INC., Gainesville, FL (US)

( * ) Notice: Subject to any disclaimer, the term of this patent is extended or adjusted under 35 U.S.C. 154(b) by 381 days.

(21) Appl. No.: 18/294,239

(22) PCT Filed: Aug. 25, 2022

(86) PCT No.: PCT/US2022/075450
§ 371 (c)(1),
(2) Date: Feb. 1, 2024

(87) PCT Pub. No.: WO2023/028553
PCT Pub. Date: Mar. 2, 2023

(65) Prior Publication Data

US 2025/0092347 A1 Mar. 20, 2025

Related U.S. Application Data

(60) Provisional application No. 63/260,545, filed on Aug. 25, 2021.

(51) Int. Cl.
*C12M 1/00* (2006.01)
*C12M 1/32* (2006.01)

(52) U.S. Cl.
CPC ............ *C12M 23/40* (2013.01); *C12M 23/12* (2013.01); *C12M 23/38* (2013.01); *C12M 29/10* (2013.01)

(58) Field of Classification Search
CPC ...... C12M 23/12; C12M 23/38; C12M 23/40; C12M 29/10

(Continued)

(56) References Cited

U.S. PATENT DOCUMENTS 5,801,055 A * 9/1998 Henderson .......... B01L 3/50255 435/297.5
2003/0215940 A1* 11/2003 Lacey ................... C12M 21/06 156/245

(Continued)

OTHER PUBLICATIONS

International Search Report and Written Opinion for WO Publication PCT/US2022/075450, dated Dec. 28, 2022.

(Continued)

*Primary Examiner* — Lydia Edwards
(74) *Attorney, Agent, or Firm* — Thomas Horstemeyer LLP.

(57) ABSTRACT

Perfusion systems compatible with 12- and 96-well plates well plates are provided. The system includes a chamber insert and a reservoir lid that couple together to fit the well plate. Each well receives an insert with compartments for media supply compartment and media collection to service media in the well. The reservoir lid includes a media supply well and a media collection port. When the system is assembled, the media supply well is in fluid communication with the media supply compartment and the media collection port is in fluid communication with the media collection compartment.

14 Claims, 15 Drawing Sheets

(58) Field of Classification Search
USPC ............................................ 435/283.1, 305.2
See application file for complete search history.

(56) References Cited

U.S. PATENT DOCUMENTS

2014/0106452 A1 4/2014 Vukasinovic
2019/0083974 A1 * 3/2019 Cambron .............. B01L 3/5025
2021/0087515 A1 3/2021 Allbritton et al.

OTHER PUBLICATIONS

Ramadan. nln vitro micro-physiological immune-competent model of the human skin 1899-1908. Royal society of chemestry. Online. Feb. 22, 2016; p. 1900-1901; material and methods, device design and fabrication; figure1. Refer to: <https://pubmed.ncbi.nlm.nih.gov/27098052/>; DOI: 10.1039/c61c00229c.

* cited by examiner

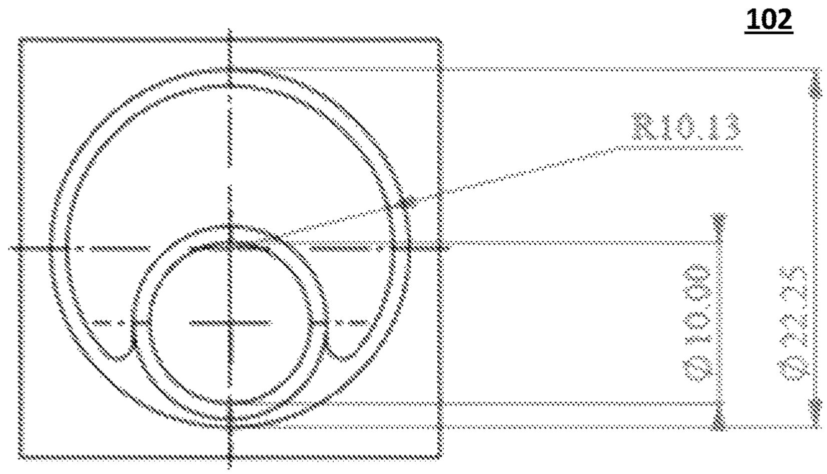
Fig. 7A
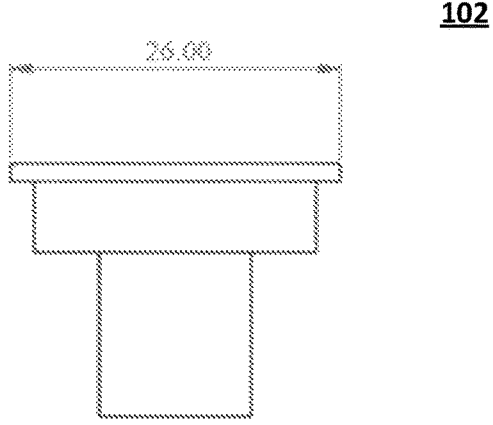
Fig. 7B
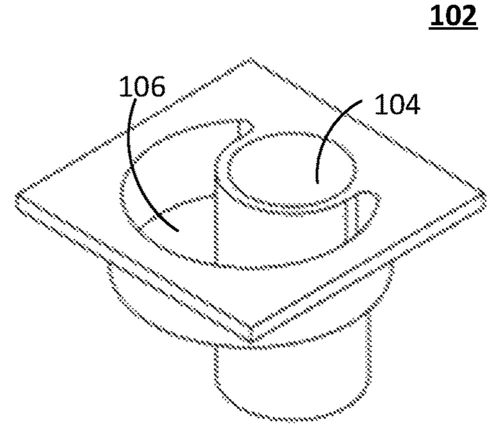
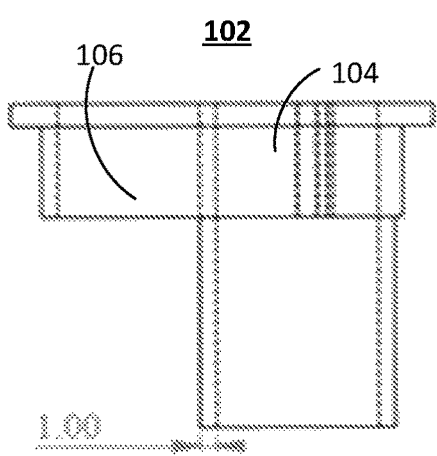

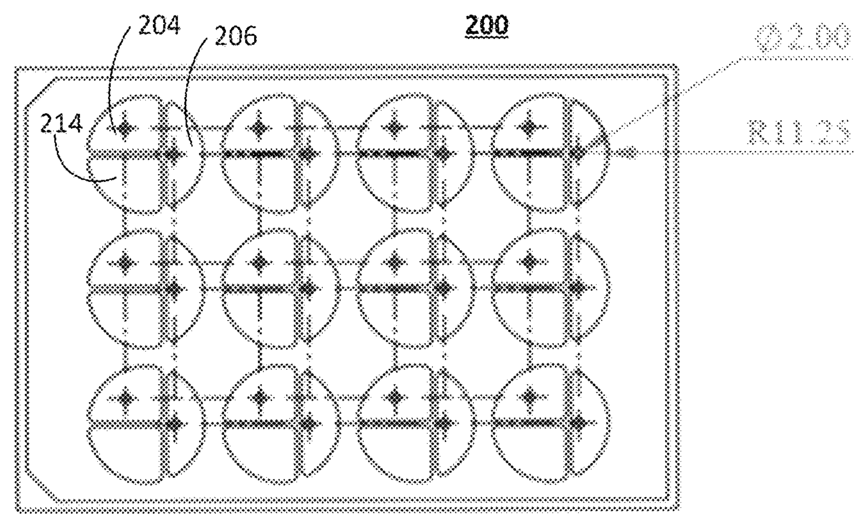
Fig. 8A
B
200
B
Fig. 8B
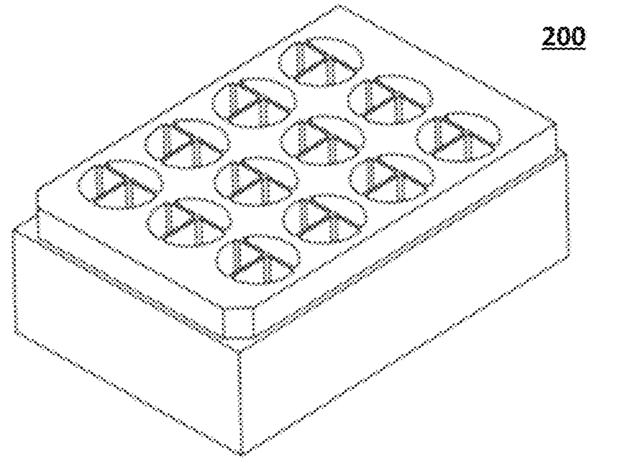
Fig. 8C
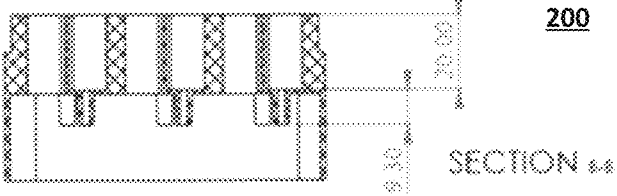
Fig. 8D

CAPILLARY-DRIVEN PERFUSION SYSTEMS AND METHODS OF USE

CROSS-REFERENCE TO RELATED APPLICATIONS

This application is the 35 U.S.C. § 371 national stage application of PCT Application No. PCT/US2022/075450, filed Aug. 25, 2022, which claims the benefit of and priority to U.S. provisional application entitled "CAPILLARY-DRIVEN PERFUSION SYSTEMS AND METHODS OF USE," having Ser. No. 63/260,545 filed on Aug. 25, 2021, which are entirely incorporated herein by reference.

STATEMENT REGARDING FEDERALLY SPONSORED RESEARCH OR DEVELOPMENT

This invention was made with government support under Grant No. W911NF-17-3-0003 awarded by the United States Department of Defense, United States Army, under a subaward from Advanced Regenerative Manufacturing Institute. The government has certain rights in the invention.

BACKGROUND

The printing or placement of biological samples (e.g., cells, cell layers, tissues) into a 3D support medium more accurately and reproducibly models the in vivo cellular microenvironment compared to conventional 2D culture. Some existing 3D cell culture techniques rely on polymer scaffolds in which cells are seeded and allowed to adhere. Once the cells are adhered to the scaffold, perfusion of growth media can begin. This method has several disadvantages: (1) cell migration is limited or precluded, (2) cell environments are defined by the structure of the polymer scaffold, (3) the experimental setup is not time-effective, and (4) does not include optical access for microscopy. In addition, cell viability for existing 3D culture methods is generally limited to several days; the passive 3D support medium cannot efficiently expel cellular waste and often hinders nutrient transport, leading to localized cytotoxic environments and subsequent cell death.

SUMMARY

Embodiments of the present disclosure provide perfusion-driven systems for cell media supply and collection.

An embodiment of the present disclosure includes perfusion systems for well plates. Systems compatible with 12- and 96-well plates are described. The system includes a chamber insert and a reservoir lid. When coupled with a well plate, the chamber insert fits into wells of the well plate and the reservoir lid forms an intimate fit on top of the well plate. Each well insert has a media supply compartment and a media collection compartment in fluid communication with one another and wherein the well insert is open at the bottom. The reservoir lid includes a media supply well and a media collection port. When the system is assembled, the media supply well is in fluid communication with the media supply compartment and the media collection port is in fluid communication with the media collection compartment.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 7A-7D provide various views of a 12-well fluid chamber insert in accordance with embodiments of the present disclosure.

FIGS. 8A-8D provide various views of a 12-well fluid reservoir lid in accordance with embodiments of the present disclosure.

Figure 1A:
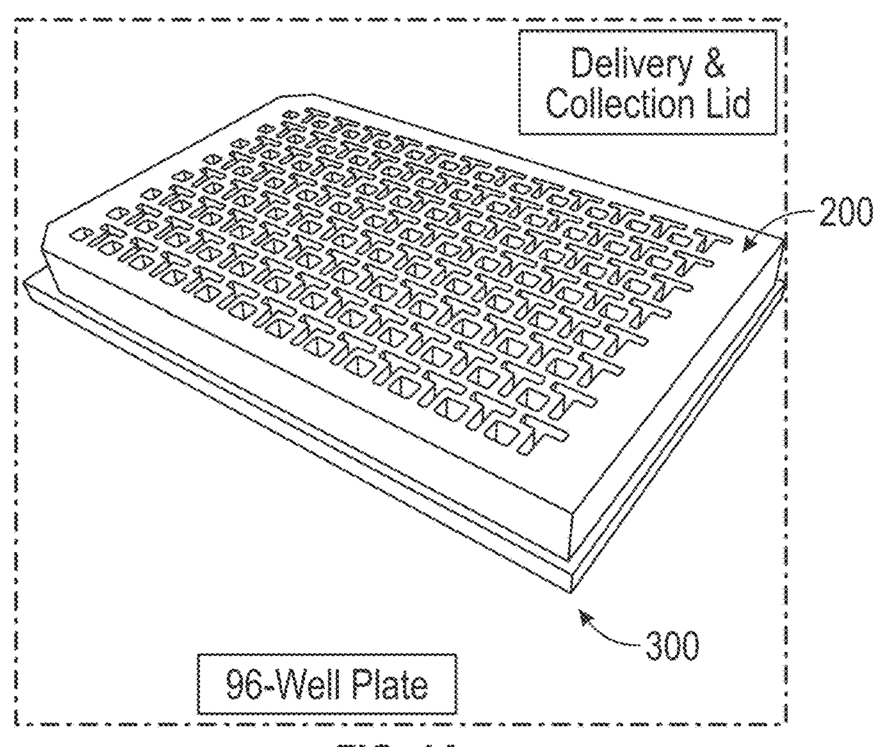
FIGS. 1A and 1B are camera images of a prototype of the 96-well perfusion system in accordance with embodiments of the present disclosure. The reservoir lid is shown in FIG. 1A, where 96 feeding wells and 96 collection wells reside. The chamber inserts, shown in FIG. 1B, are placed in the wells of the well plate and the reservoir lid is placed on top. The plastic lid that comes with the polystyrene well plate is placed on top of the reservoir lid during incubation periods.
Figure 1B:
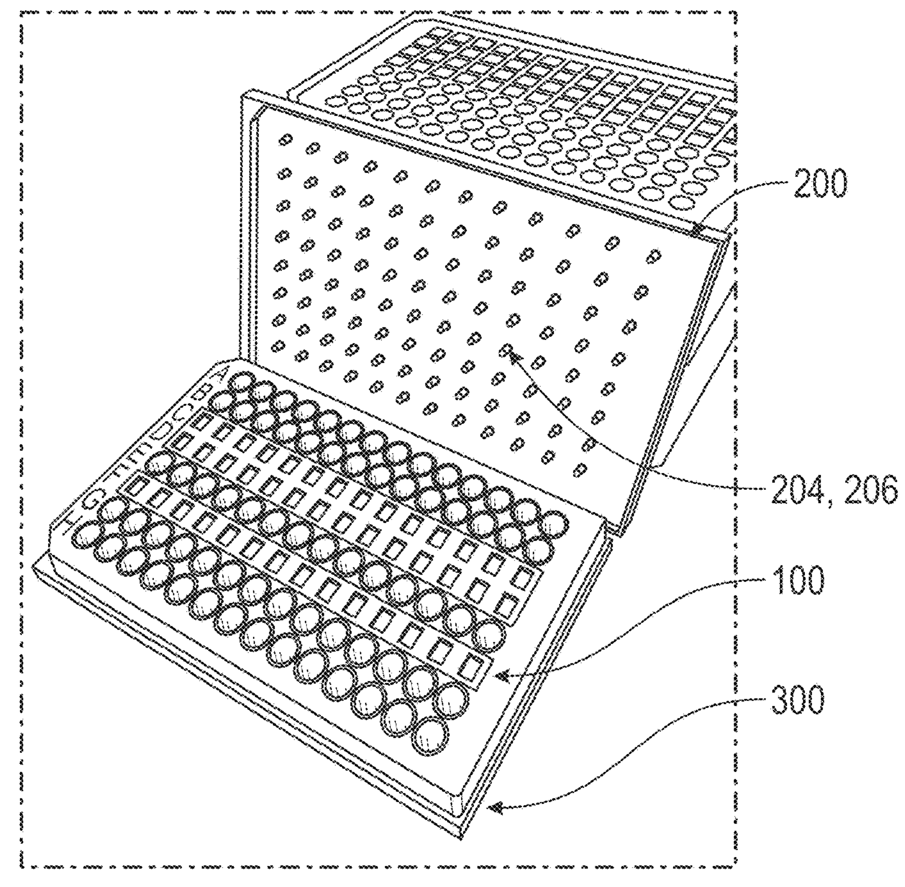
Figure 2A:
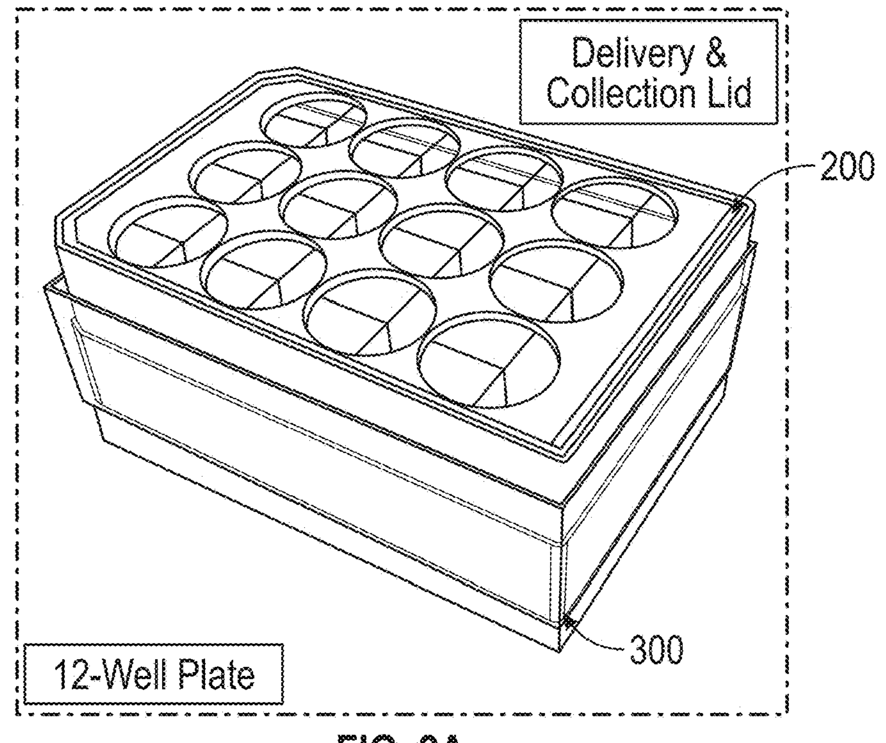
FIGS. 2A and 2B are camera images of a prototype of the 12-well perfusion system in accordance with embodiments of the present disclosure. While this system operates differently from the 96-well system, it has the same basic components. The reservoir lid is shown in FIG. 1A, where 12 feeding wells and 12 collection ports reside. The chamber inserts, shown in FIG. 2B, are placed in the wells of the well plate and the reservoir lid is placed on top. The plastic lid that comes with the polystyrene well plate can be placed on top of the reservoir lid during incubation periods.
Figure 2B:
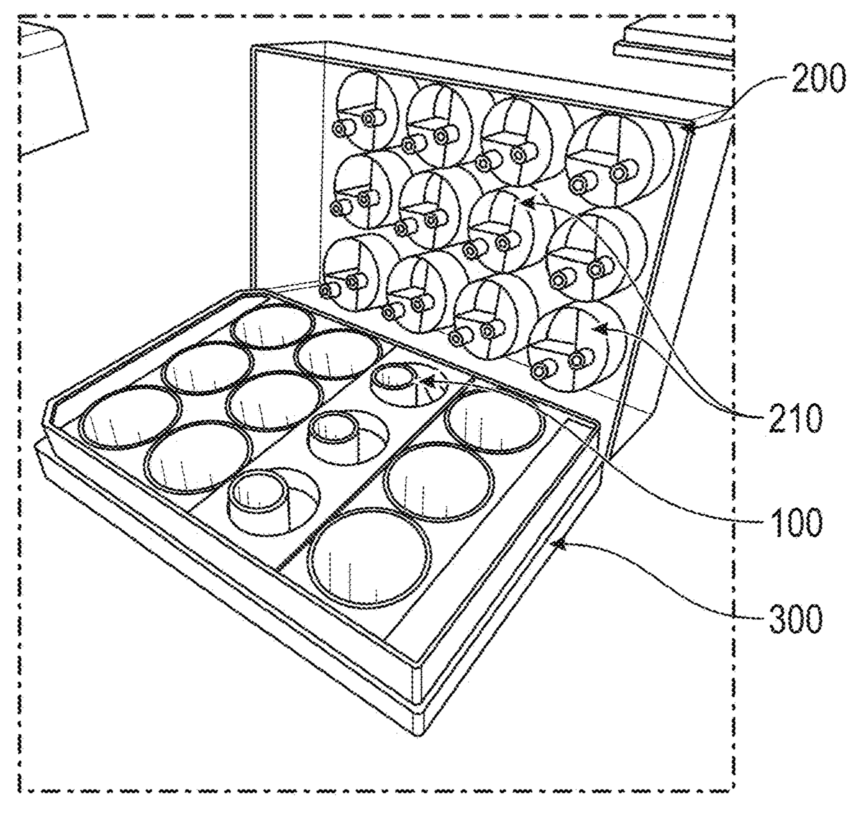

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the products disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

GENERAL DISCUSSION

In accordance with the purpose(s) of the present disclosure, as embodied and broadly described herein, embodiments of the present disclosure, in some aspects, relate to perfusion systems and methods for using perfusion systems The present disclosure includes a perfusion system for a well plate. Advantageously, the system can be used with commercially available well plates. The perfusion system can be made from sterile materials designed to be consumables (e.g. single use disposables) or can be made from durable materials that can be sterilized and reused.

Embodiments of the present disclosure include a perfusion system as above, wherein the system includes a chamber insert and a reservoir lid. When coupled with a well plate, the chamber insert fits into wells of the well plate and the reservoir lid forms an intimate fit on top of the well plate. The chamber insert includes a plurality of well inserts, each well insert having a media supply compartment and a media collection compartment. The compartments are in fluid communication with one another and open at the bottom. The reservoir lid comprises a media supply well and a media collection port. When the chamber insert and reservoir lid are assembled, the media supply well in the lid is in fluid communication with the media supply compartment of the chamber insert and the media collection port is in fluid communication with the media collection compartment.

In some embodiments, the perfusion system is configured to be used with a 96-well plate. In other embodiments, the perfusion system is configured to be used with a 12-well plate. As can be envisioned by one of ordinary skill in the art, the perfusion systems described herein can be modified to be used with well plates of various configurations.

In some embodiments, multiple well inserts are connected. For example, a strip of multiple well inserts can be manufactured as a single unit to correspond to a row or column of wells in a well plate (e.g., a strip of 12 wells to correspond to a 96-well plate, a strip of 4 wells to correspond to a 12-well plate, a strip 3 wells to correspond to a 12-well plate). In other embodiments, the well inserts can be individually removably connected to one another. In some embodiments, strips of well plates can be removably connected to one another. In other embodiments, an array of well inserts can be connected or manufactured as a single unit such that when the chamber insert is inserted into a well plate, all of the wells are simultaneously fitted with a well insert.

The perfusion system described herein has a low profile such that when assembled with a well plate, the chamber inserts and reservoir lid do not significantly increase the height of the well plate. The lid supplied with the well plate fits atop the reservoir lid of the perfusion system, providing a protective layer to prevent unwanted contaminants from entering the well plate through the ports in the reservoir lid.

Advantageously, the perfusion system described herein allows for nutrient delivery and export using capillary forces to gently drive fluid flow. The two-part capillary-driven bioreactor utilizes gravity driven flow into a traditional well plate. As the fluid rises within the well, it comes into contact with a narrow channel that is connected to a larger, three-dimensional capillary network. Liquid is first pulled into the narrow channel by capillary forces, then is further pulled into the 3D capillary network like a sponge, aspirating the used media from within the well. Afterwards, the aspirate can be pipetted or collected by other means. Through this process, the need for mechanical pumps and electrical components is negated, providing a low-cost, low-maintenance solution instead. Advantageously, the system described herein is a macrofluidic system that uses capillary forces to aspirate media. Unlike microfluidic systems which rely on passive flow through narrow channels, the present system actively pulls fluid through the chamber using a 3D capillary network at the outlet.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Described herein are two perfusion systems designed to work with a microgel-based 3D culture media. In addition to the 96-well format, described is a system for use with 12-well plates. Each of the designs comprise two separate parts: (1) a chamber insert 100 that separates each well into a printing chamber/feeding zone and a media collection zone; (2) a reservoir lid 200 that contains wells for supplying media and wells or ports for collecting media (FIGS. 1A, 1B, 2A, and 2B). To use either the 96-well or the 12-well system, the chamber inserts 100 are placed in well plates 300, microgel-media is deposited at the bottom of the wells, and tissue printing is performed inside the media supply compartment (also called a printing chamber). The printing chamber is the volume in the bottom of each well that is not occupied by the components of the system. The reservoir lids are then put in place, and feeding reservoirs are filled. This design allows the user to control media composition over time, exchange media at will, or adapt to automated fluidic systems. As shown in the results below, both designs are capable of exchanging at least 1 mL per day per well.

96-Well Perfusion System

Figure 3:
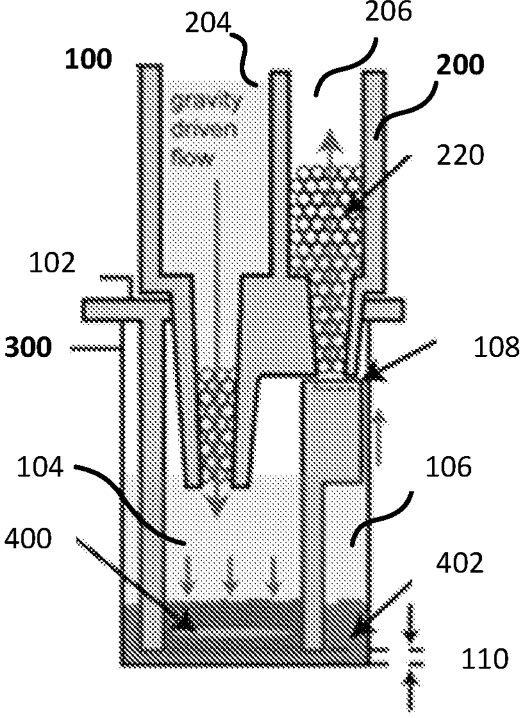
FIG. 3 provides a schematic illustrating one well of the 96-well perfusion system in accordance with embodiments of the present disclosure. Before placing the reservoir lid, microgel based media is loaded into the well, the chamber insert is positioned, and 3D bioprinting performed. Following the printing process, the reservoir lid is put into place and perfusion is initiated.

In the 96-well plate design, liquid exchange is achieved through gravity-driven inflow and capillary-driven outflow, in which a combination of capillary channels and a 3D capillary network pull media from the inlet side of the chamber insert 100 into the collection well of the reservoir lid 200. The 400-micron×100-micron capillary channel 108 shown in FIG. 3 is a channel cut into the insert between the bottom of the lid well and the top of the collection chamber 106, and the capillary along the wall of the plate is formed by a precisely measured gap 110 that allows wetting of the insert. The compact nature of the system leverages capillarity. In FIG. 3, arrows show the direction of the inflow and outflow. In short, gravity drives flow passively through the media supply well 204 in the reservoir lid 200, then into media supply compartment 104 in well insert 102 to reach the sample 400 (3D printed liver microtissue in a PEG microgel 402 in this particular example). The well insert 102 is precisely measured to form a gap 110 between the open bottom of media supply compartment 104 and the bottom of the well 302 in well plate 300 such that the media supply compartment 104 and the collection chamber 106 are in fluid communication with one another. The gap 110 can be about 100 μm high. The liquid flows into gap 110 and climbs up between capillary gaps formed between the sidewalls of the well insert 102 and the sidewalls well 302, where the capillary action further pulls the fluid through the capillary channel 108 into the media collection port 206 in the reservoir lid 200. Media collection port 206 can be filled with a 3D capillary network 220 through which the liquid is pulled. A 3D capillary network 220 can also be inserted in media supply well 204. The size of the capillary gaps, channels, and 3D capillary networks control the flow rate.

The 3D capillary network can take a number of different forms. Both packs of polyacrylamide chromatography beads and open-cell polyurethane foam inserts were tested. Both worked well to pull liquid media from the bottom chamber to the collection chamber, though tissue tests were ultimately performed using polyeurethane open-cell foam inserts. This general design approach was pursued with the long-term goal of mass-producing the system at low-cost while ensuring the product required no specialized equipment like electrically powered pumps or tubing. The prototype system was machined from aluminum (reservoir lid)

and Delrin® acetal resin, also known as acetal homopolymer (chamber inserts). For mass production, both parts can be made from such as polystyrene and supplied in sterile packaging. The entire system can be supplied to users as low-cost consumables, much like well-plates are supplied and used ubiquitously in cell culture.

To facilitate performing tests on fewer than 96-wells at a time, and to reduce costs, the chamber inserts were designed as 12-well strips; eight strips would fill all 96 wells (FIGS. 4A-4D). Acetal resin prototypes were re-used between tests; cleaning and sterilization was achieved through a detergent wash followed by an ethanol wash. As described above, these strips may be supplied to users in sterile packaging; they can be "disposable" like typical laboratory consumables made from such as polystyrene. Alternatively, reusable chamber inserts that may be sterilized can also be envisioned by one of ordinary skill in the art.

Advantageously, the strip design facilitates modularity and fits standard 96-well plates. The shown embodiments are designed for flat-bottomed wells, but as can be envisioned by one of ordinary skill in the art, inserts as provided herein could be modified to work with other well shapes (e.g., v- or u-shaped bottoms). Printing and collection volumes are divided by the chamber insert. The chamber insert guides fluid from feeding to the collection reservoirs in the lid.

Figure 4A:
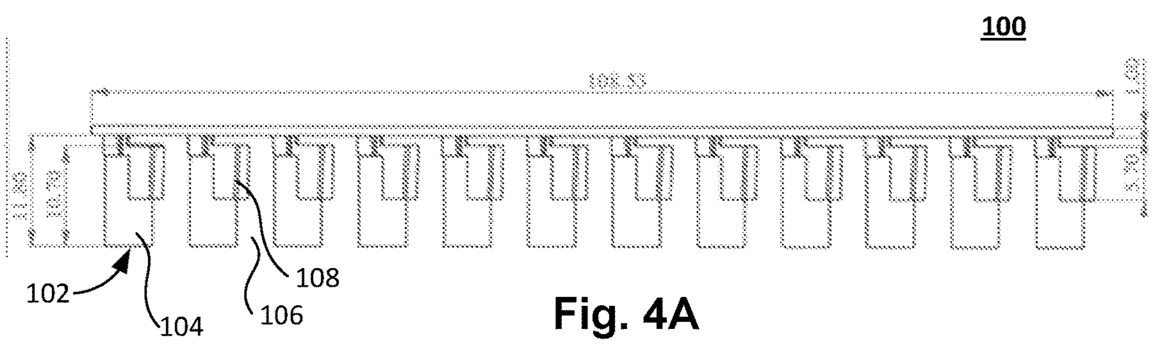
FIGS. 4A-4D provide illustrations of a 96-well chamber insert system in accordance with embodiments of the present disclosure. Units in mm.
Figure 4B:
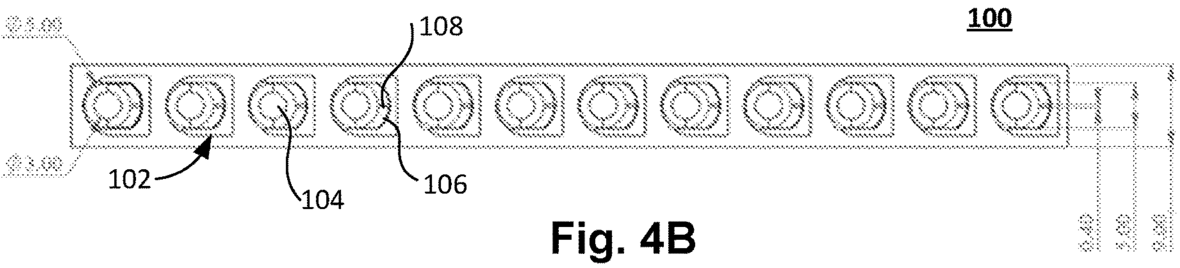
Figure 4C:
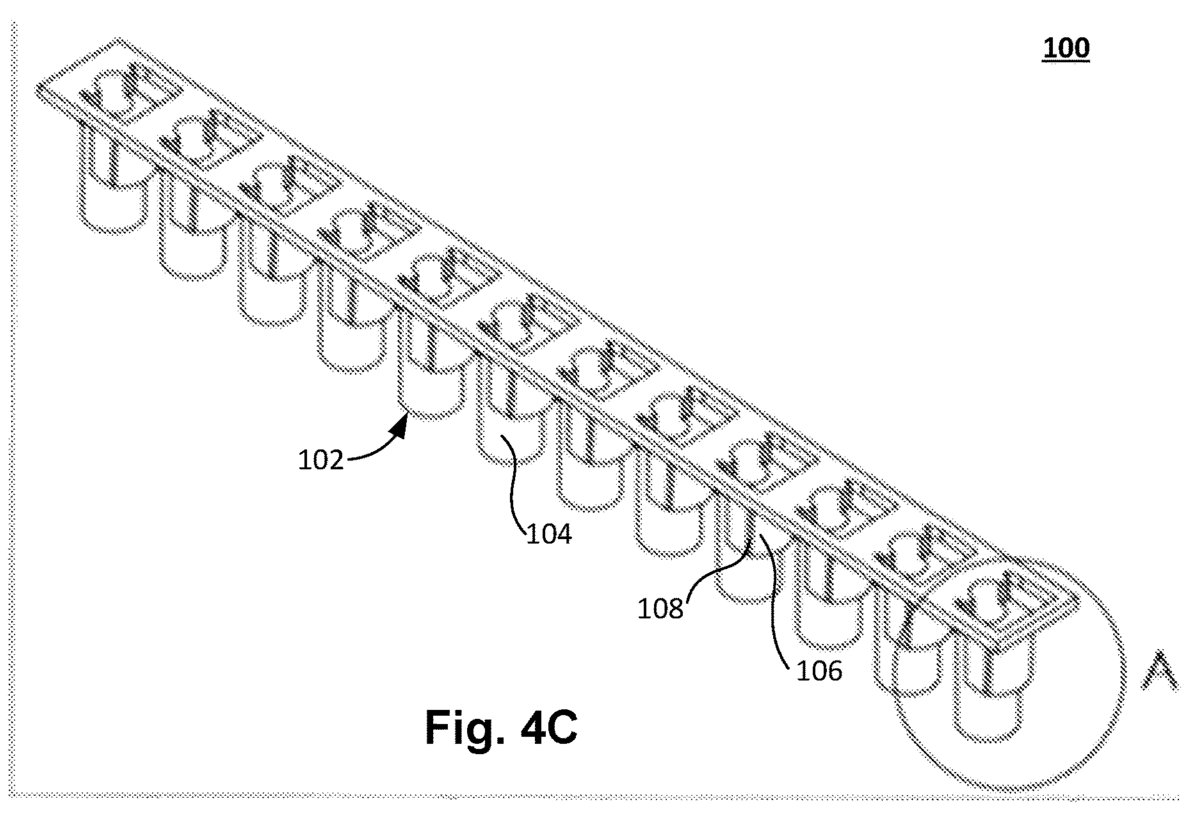
Figure 4D:
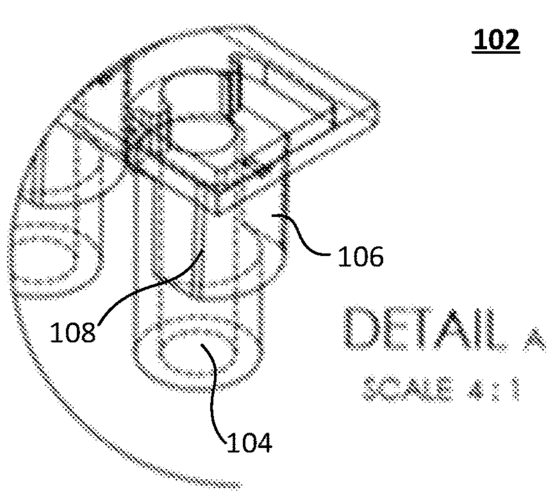

In FIGS. 4A-4D, an example of the chamber insert 100 with 12 well inserts 102 is shown. This particular embodiment is a strip format having 12 well inserts, corresponding to one of eight rows of wells in a 96-well plate (not shown). The media supply compartment 104 is a cylindrical shape having an open bottom. Well insert 102 comprises a quasi-lunate shape that wraps around a portion of the media supply compartment 104 that, once inserted in a well, creates a gap serving as the media collection compartment 106 (also referred to as a media collection chamber). FIG. 4A shows the chamber insert 100 from the side. FIG. 4B shows the chamber insert 100 from the top. The media collection compartment 106 connects fluid to the reservoir lid 200 via a capillary channel 108 cut into the quasi-lunate shape from the base to the top. FIG. 4C is a perspective view of the chamber insert 100 and FIG. 4D is a detail view of the circled well insert 102 shown in FIG. 4C. The dashed line in FIG. 4D (Detail A) corresponds to the inner wall of the media supply compartment (also called a printing chamber). Media flows down, out, and then spontaneously climbs the wall along the side and into the 400×100 micron channel 108 and then into the capillary tube in the lid. The overall height of the media collection chamber insert is 12.80 mm. The exterior diameter of the media collection compartment is 5.00 mm and the interior diameter is 3.00 mm. The height of the media supply compartment is about 11.80 mm, and the height of the media collection compartment is about 5.70 mm.

Figure 5A:
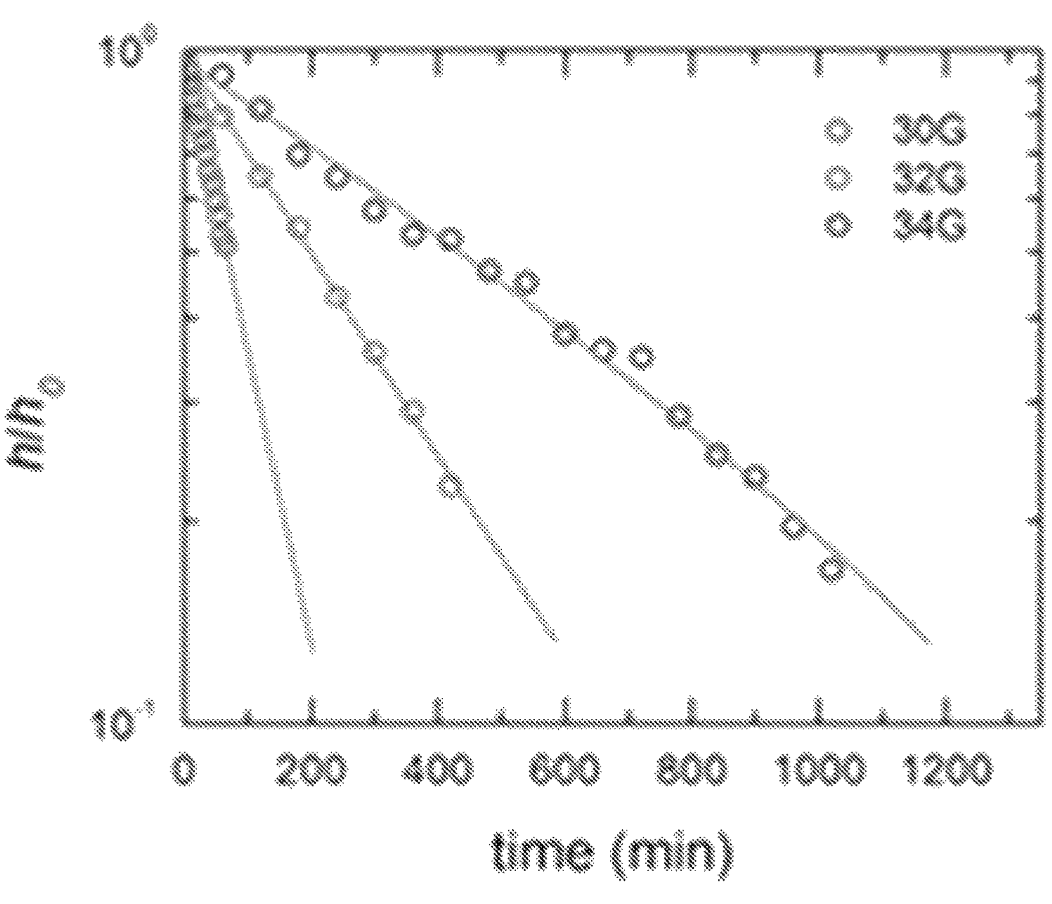
FIGS. 5A-5B are graphs showing that the height of the liquid head in the feeding chamber over time decreases exponentially, as predicted by gravity driven flow through a narrow restriction. The time-constant can be quantitatively predicted from the Poiseuille-Hagen equation. Fluid exchange rates exceeding 1 mL/day can be achieved with this approach.
Figure 5B:
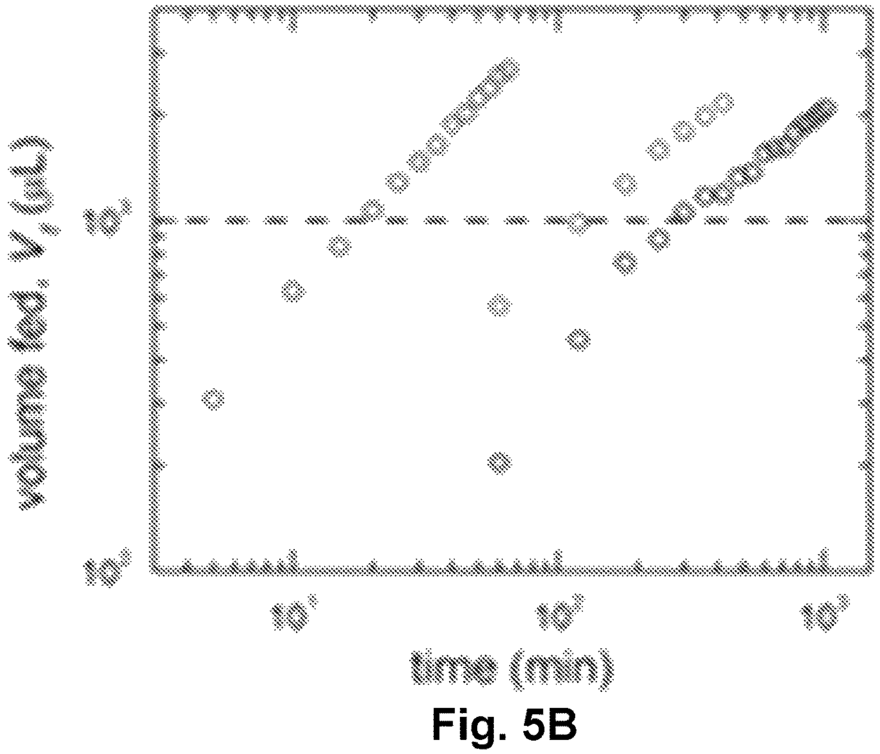

The rate of capillary-driven rise of fluid into the collection chamber is very fast; it can keep up with media infusion rates of at least 20 L/s. Thus, the system was designed to break the capillary bridge between the chamber insert and the well-plate wall when the media level falls below a pre-determined height (see FIG. 3). Thus, to control the rate of media flow, the fluid reservoir lid was designed to restrict the rate of fluid delivery into the well. By leveraging gravity-driven flow through restrictions of known size and shape, the flow profile can be quantitatively predicted over time (FIGS. 5A-5B). For the tests, blunt syringe needles having known diameters were affixed to the outlets of the media supply compartments 104. Predictably, as shown in FIG. 5A, needle gauge controls flow rate (30 G, 32 G, 34 G) and that the systems described herein are able to meet the feeding volume requirement of greater than 1 mL/day. The liquid head height was calculated using $$h(t) = h_0 e^{-t/\tau}$$

where τ is predicted from flow through pipe and gravity and volume is a product of h and well area.

Advantageously, the chamber insert strips were designed to be very low profile, as seen in FIG. 1, allowing the fluid reservoir lid to fit onto the well-plate, just like the polystyrene lid provided by the manufacturer. Likewise, the top portion of the fluid reservoir lid was designed to accommodate the polystyrene lid supplied with the commercially available well-plate. Thus, when the entire system is assembled it is very compact and resembles the original well-plate, but with an extra layer between the bottom plate and the polystyrene lid. The fluid reservoir lid contains 192 wells—96 for delivering media and 96 for collecting media (FIG. 6). Filling all the wells in the plate can therefore be conveniently achieved using a multi-tip micropipette. For efficient collection of perfusate, while the open-cell foam inserts were manufactured by hand, sterile arrays of cylindrical foam "posts" could be easily manufactured, allowing a user to collect from all the wells simultaneously by inserting the entire post array into the collection well array. Similarly, the fluid was extracted from the foam inserts through centrifugation. This procedure is easily scaled to 96 wells at a time using the "foam post array" design, in which the entire array of posts are inserted into a new 96 well plate and centrifuged all at once, drawing the fluid out of the foam posts into the wells for assaying. This approach could be taken to simultaneously load all the wells in an ELISA plate for assaying. A commercially available foam post array would be disposable and supplied in sterile packaging.

Figure 6A:
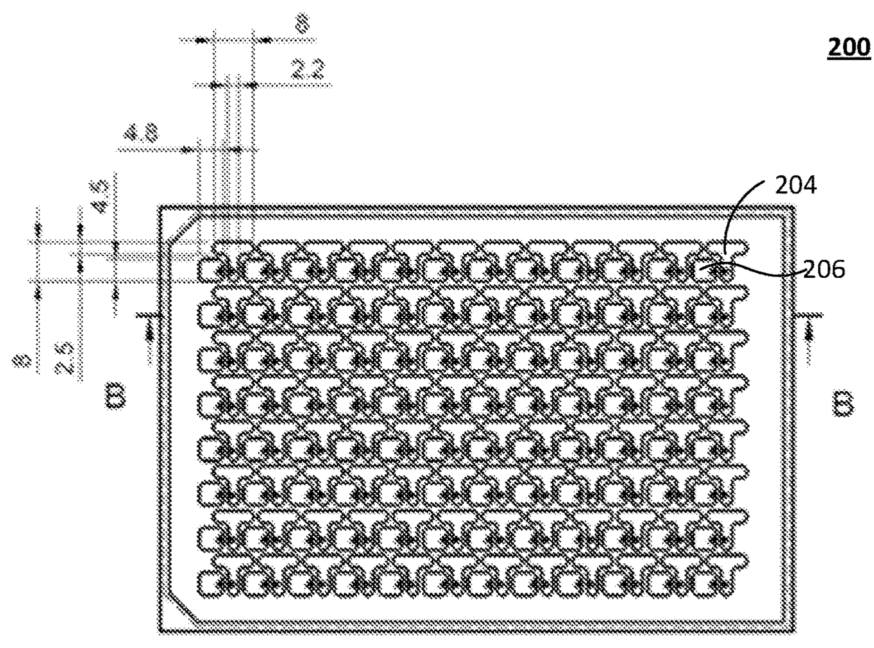
FIGS. 6A-6E provide various views of a 96-well fluid reservoir lid in accordance with embodiments of the present disclosure.
Figure 6B:
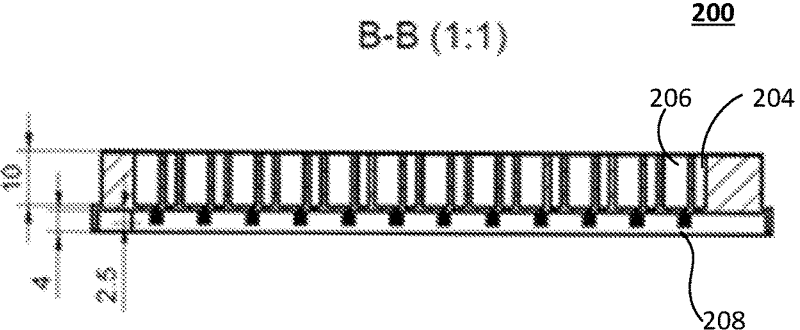
Figure 6C:
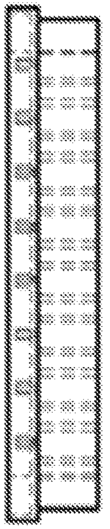
Figure 6D:
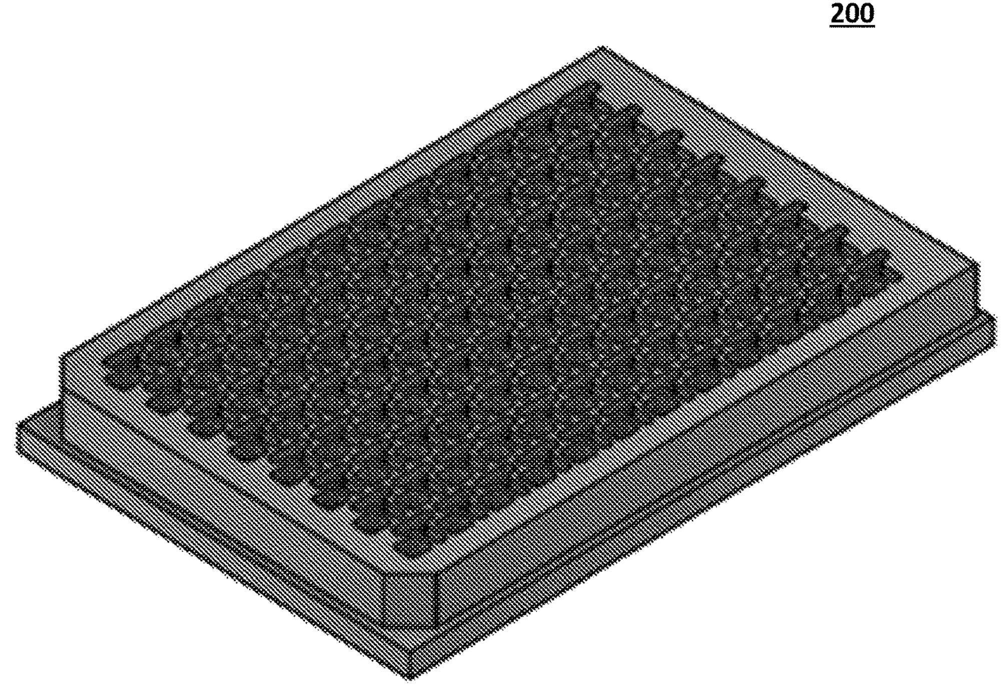
Figure 6E:
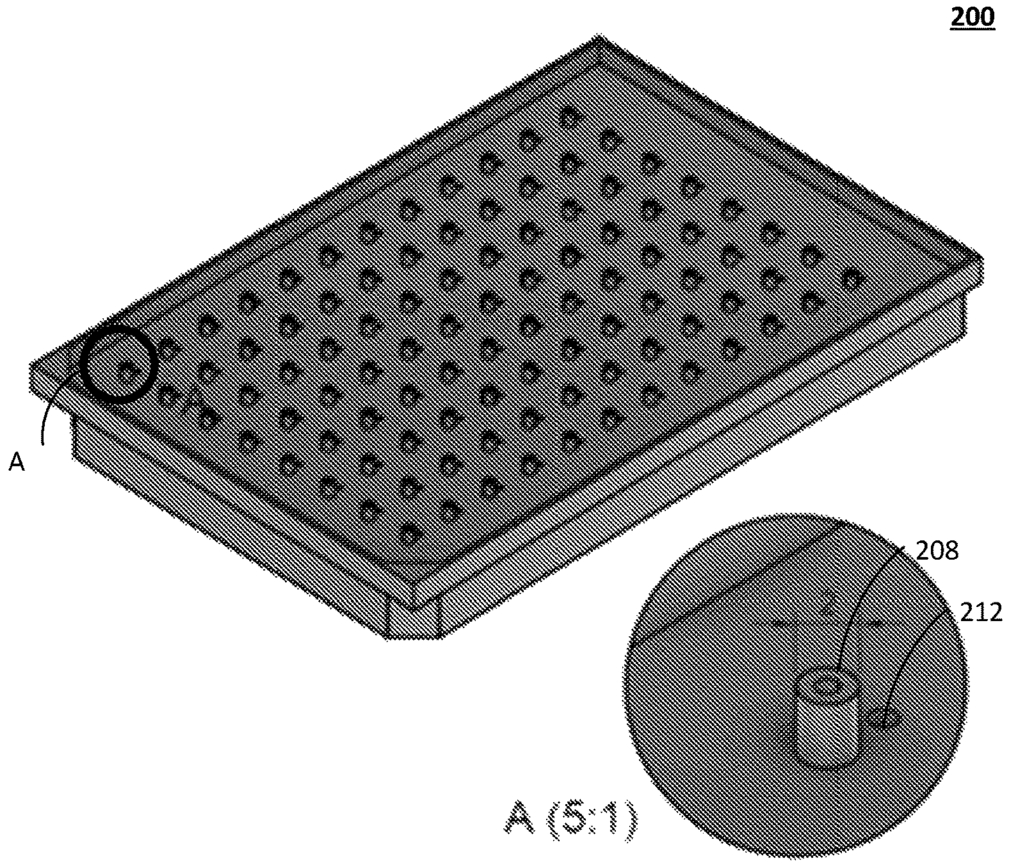

As shown in FIGS. 6A-6E, the fluid reservoir lid 200 allows for separated media delivery 204 and collection wells 206. Each well has its own media delivery chamber 204 for feeding (T-shaped) and its own collection chamber 206 (square-shaped). FIG. 6A shows fluid reservoir lid 200 from the top, and FIG. 6B shows a side view through B-B of FIG. 6A. FIG. 6B is a side view. FIG. 6D shows a top view and FIG. 6E shows a bottom view. Delivery nozzles can control the flow rate, and can be attached to the media delivery holes 212 shown in detail A (FIG. 6E). In some embodiments, hollow, tubes (e.g., stainless steel) that fit snugly into the holes can be coupled with the media delivery holes 212 to deliver media. A precision collection port 208 is coupled to the chamber inserts. The precision collection port 208 projects from the underside of the reservoir lid to contact the chamber insert and fluidly communicates with the 400×100 micron channel 108 when fitted to the chamber insert (not shown). Dimensions of the components in mm of the fluid reservoir lid 200 can be found in FIGS. 6A-6E.

12 Well Perfusion System

The 12 well-system works in the same way as the 96-well system; chamber inserts provide an impermeable wall that guides fluid downward through the tissue, outward at the bottom of the wells, and back up toward a collection chamber; a fluid reservoir lid controls gravity-driven flow into the well plate and capillary-driven flow back up into a collection well (FIGS. 7A-7D, 8A-8D). In contrast to the 96-well design, there is sufficient open space in 12-well design to provide an open media collection port 206 so that the user can directly collect perfusate with a pipette without needing to utilize the capillary driven up-flow. This feature provides more freedom to a user doing low-throughput work. Similarly, since addressing 12 wells one at a time by hand is not burdensome like doing so with 96 wells, one can envision the user manually attaching the sterile syringe needles to the underside of the fluid reservoir lid. Thus, embodiments of the design include press-fit mounts 210 for attaching needles, just like the end of a syringe. One press-fit mount 210 is provided per well (see FIG. 2B). This design would allow a user to choose a flow-profile by choice of needle, rather than having to purchase a lid with pre-manufactured constrictions that would otherwise set the flow profile. The chamber inserts enable division of the printing and collection volumes, and guide fluid from feeding to collection reservoirs. As with the 96-well system, the 12-well chamber inserts fit standard plates. The dimensions of the chamber inserts enable either manual or automatic collection. FIGS. 7A-7D show top, side, perspective, and section views, respectively of a well insert 102 for a chamber insert 100 compatible with a 12-well plate. FIGS. 8A-8D show a 12-well fluid reservoir lid 200 from top (FIG. 8A), side (FIG. 8B), perspective (FIG. 8C), and section views (8D) (through B-B of FIG. 8B), respectively. FIG. 8A shows the media collection wells 206, media delivery wells 204, and on open segment 214 for use with manual feeding when controlled perfusion is not desired.

Testing the 96-Well Perfusion System on 3D Printed Liver Microtissues

To investigate the effects of flowing different volumes of media across 3D printed liver microtissues, the 96-well perfusion system was tested on disk-shaped structures made from HepaRG hepatocytes embedded in 1 mg/mL collagen-1 matrix. Here, the microgel 3D printing and culture medium is prepared by performing a solvent exchange from PBS, in which the microgels are stored, to complete Williams' E media. After the solvent exchange, the microgels are centrifuged at 2000 rpm for 20 minutes. Most excess supernatant fluid is removed, leaving equal volumes of packed microgels and supernatant. The microgels are pipette mixed to create a homogeneous mixture and a volume of 50 mL of this dispersion is transferred to each well of a 96 well, glass bottomed plate. An additional 110 mL of liquid media is added. HepaRG and collagen-I mixtures are printed into disks of 1.75 mm in diameter into select wells of the 96 well plate. The printed tissues are incubated for 15 hours at 37° C. and 5% $CO_2$ prior to the first media exchange.

Before the first media exchange, the reservoir lid is placed atop the 96 well plate. In the tests described here, media exchanges were performed three times per day for six additional days beyond the first day of pre-incubation. For these tests an 18-gauge needle was fixed to the outlet of each feeding well to control media flow rate, allowing each exchange to take just a few seconds; finer gauge needles can be used to deliver continuous perfusion. During each media exchange, perfusion is rapidly driven by gently placing a sterile 3D capillary network made from open cell polyurethane foam into the aspiration well where it comes into contact with the aspiration capillary. The liquid bridge created at this point of contact supports capillary flow from the lower collection chamber into the upper collection reservoir in the lid. The polyurethane foam devices were pre-calibrated to collect known volumes of media during each exchange cycle. For these experiments, the foam devices were weighed before and after media collection to precisely quantify the volume of media exchanged. Equivalent volumes of fresh media were then added to the feeding well to maintain a constant total sample volume. To examine the effect of daily exchange rate on microtissue performance, full growth media was delivered at total daily rates of 1.0 mL/day, 0.50 mL/day, and 0.25 mL/day. Similarly, the effect of glucose concentration on microtissue performance was examined by exchanging fresh media at 0.225 mL/day at glucose concentrations of 2.0 g/L, 1.0 g/L, and 0.5 g/L. In order to collect media during each exchange, it is important to wet the surface of the aspiration components prior to feeding to create the capillary bridges that pull media through the system. After the samples are collected, they are frozen in a −80° C. freezer. After each feed, the foam devices are washed in a detergent solution and sterilized in 100% ethanol.

Figure 9:
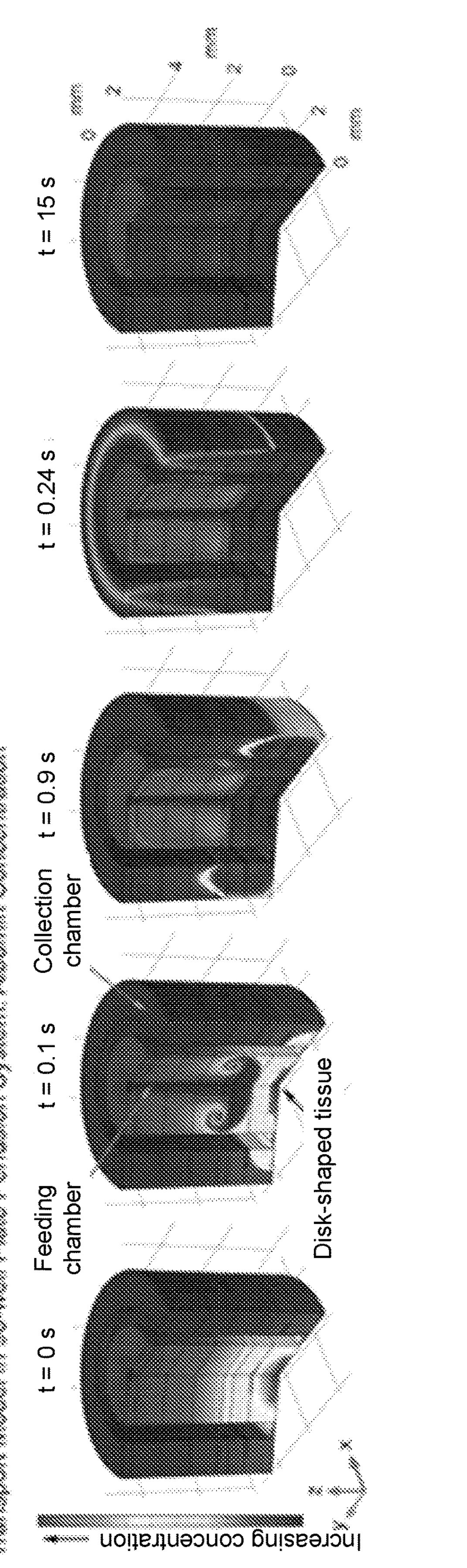
FIG. 9 provides computational models of snapshots of the albumin concentration distribution in a well from the 96-well perfusion system in accordance with embodiments of the present disclosure. After four hours of static culture, a concentrated cloud of albumin is seen around the tissue with very little albumin having diffused under the chamber insert wall into the collection chamber. Immediately after initiating perfusion, the cloud of albumin is driven into the collection chamber with some recirculating flow occurring within the feeding chamber. Within 15 seconds, most of the albumin is flushed from the system.

Previous control measurements of media exchanged in static culture showed that Albumin and Urea content was the same in the microgel as in the supernatant media. By contrast, in the present perfusion system the barriers between the different chambers have a significant impact on molecular transport. Thus, to determine albumin and urea synthesis rates from concentration measurements of media collected during perfusion tests, a computational model of the perfusion systems was developed that includes a model tissue producing albumin and urea at chosen rates (see Computational Model Methods and details below). The model computes both convective flow and molecular transport throughout the culture chamber. Snapshots of the modeled albumin distribution in the well after four hours of static culture show a concentrated cloud around the tissue with very little albumin having diffused under the chamber insert wall into the collection chamber. Immediately after initiating perfusion, the cloud of albumin is driven into the collection chamber with some recirculating flow occurring within the feeding chamber. Within 15 seconds, most of the albumin is flushed from the system; the molecular flux across the outlet is monitored and the total mass of albumin exiting the outlet is computed (FIG. 9). The full 24-hour cycle including the three media exchanges was simulated using this computational model, reproducing experimental protocols.

Figures 10A, 10B:
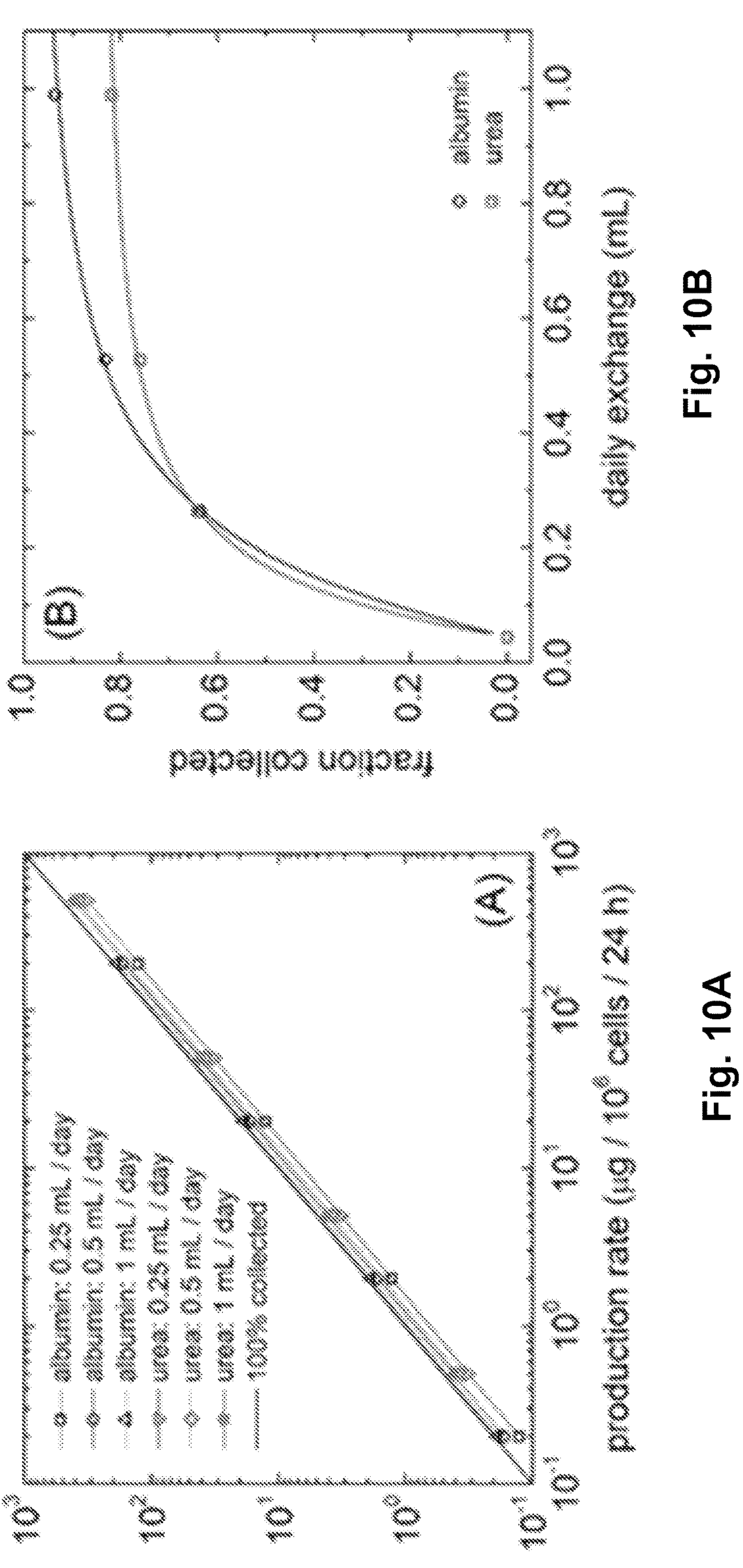
FIG. 10A is a computational model showing that for any overall media exchange rate, the total mass of molecules collected scales perfectly linearly with production rate, as expected, but a significant fraction of molecules is not collected.
FIG. 10B shows that the fraction of molecules collected varies non-linearly with daily exchange rate and differs between molecular species. A lower proportion of urea is collected because it more rapidly diffuses back into the feeding well between media exchanges, while albumin remains closer to the tissue and is more readily flushed out into the collection chamber.

To determine the proportion of albumin or urea collected relative to total daily production, experiments for tissues producing these molecules at four different rates were simulated. For any overall media exchange rate, the total mass of molecules collected scaled perfectly linearly with production rate, as expected (FIG. 10A). However, some proportion of molecules were left behind in the culture well and that this proportion differed based on molecular species and on total exchange rate. Plotting the fraction of molecules collected versus daily exchange rate, all data points for a given exchange rate and molecular species collapse, as expected from the linear relationship between collected mass and produced mass. The fraction of molecules collected varies non-linearly with daily exchange rate and differs between molecular species. Even at high flow rates, a lower proportion of urea is collected because it more rapidly diffuses back into the feeding well between media exchanges, while albumin remains closer to the tissue and is more readily flushed out into the collection chamber (FIG. 10B).

Figure 11B:
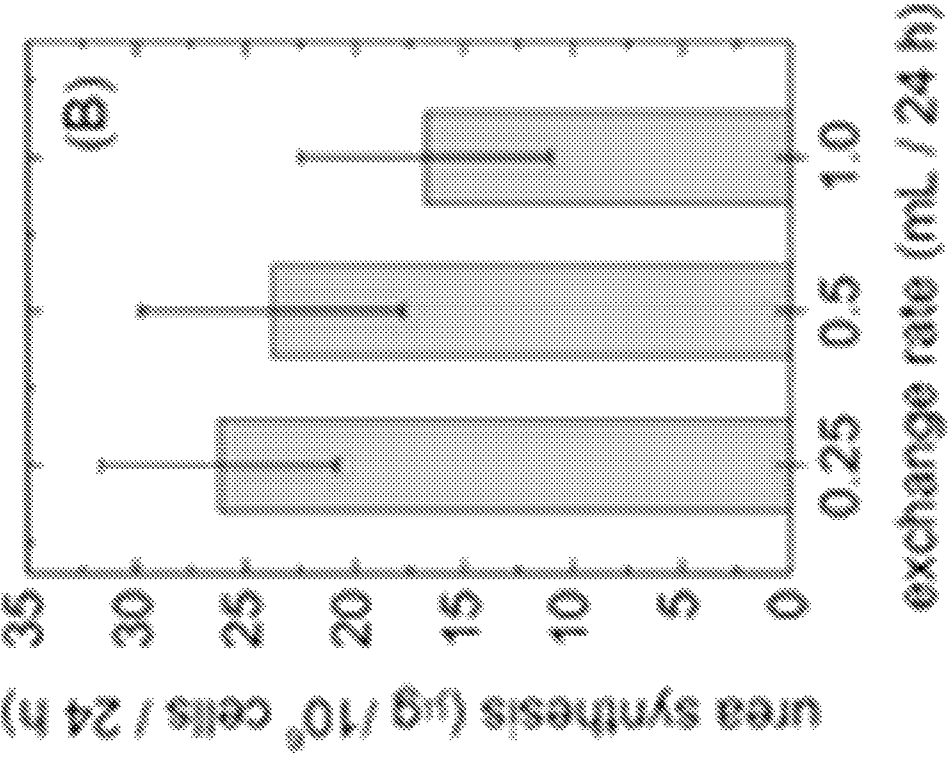
FIGS. 11A-11D provide graphs of albumin and urea production by 3D printed HepaRG tissues, measured after 6 days of perfusion at different exchange rates and in media having different levels of glucose. Shown is a weak increase in albumin secretion with media exchange rate (FIG. 11A) and a weak decrease in urea synthesis with increasing exchange rate (FIG. 11B). While albumin secretion was found to be strongly sensitive to glucose levels (FIG. 11C), no clear trend was seen for urea synthesis (FIG. 11D).
Figure 11A:
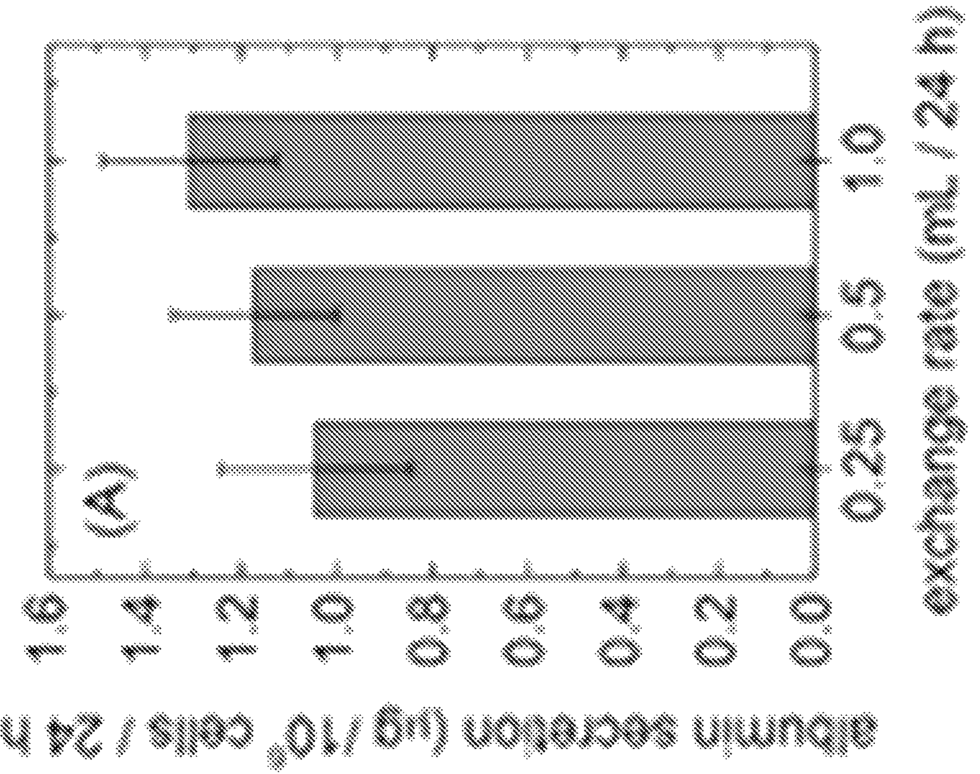

Leverage the results from the computational model to analyze the experimental data collected in these perfusion tests, the experimental albumin and urea concentrations were measured using the protocols developed during this project and described in previous reports. Due to careful measurement of the volume of media collected throughout the exchange cycles, the total mass of each molecular species collected could be computed. As part of these tests, harvested tissues (n=3 for 0.5 and 1.0 mL/day tests; n=6 for 0.25 mL/day test) were used to determine the number of cells per tissue using a pico-green assay. Together, this information determines the mass of albumin or urea per 106 per day collected in the experiments. Using the data plotted in FIG. 10B, the masses produced by the tissues were converted from albumin and urea masses collected. Plotting these results versus exchange rate shows a weak increase in albumin secretion with media exchange rate, though the differences are within one standard error interval of one another. Similarly, there is a weak decrease in urea synthesis with increasing exchange rate, with the data points also being within one standard error interval of one another (FIGS. 11A-11B).

Figure 11D:
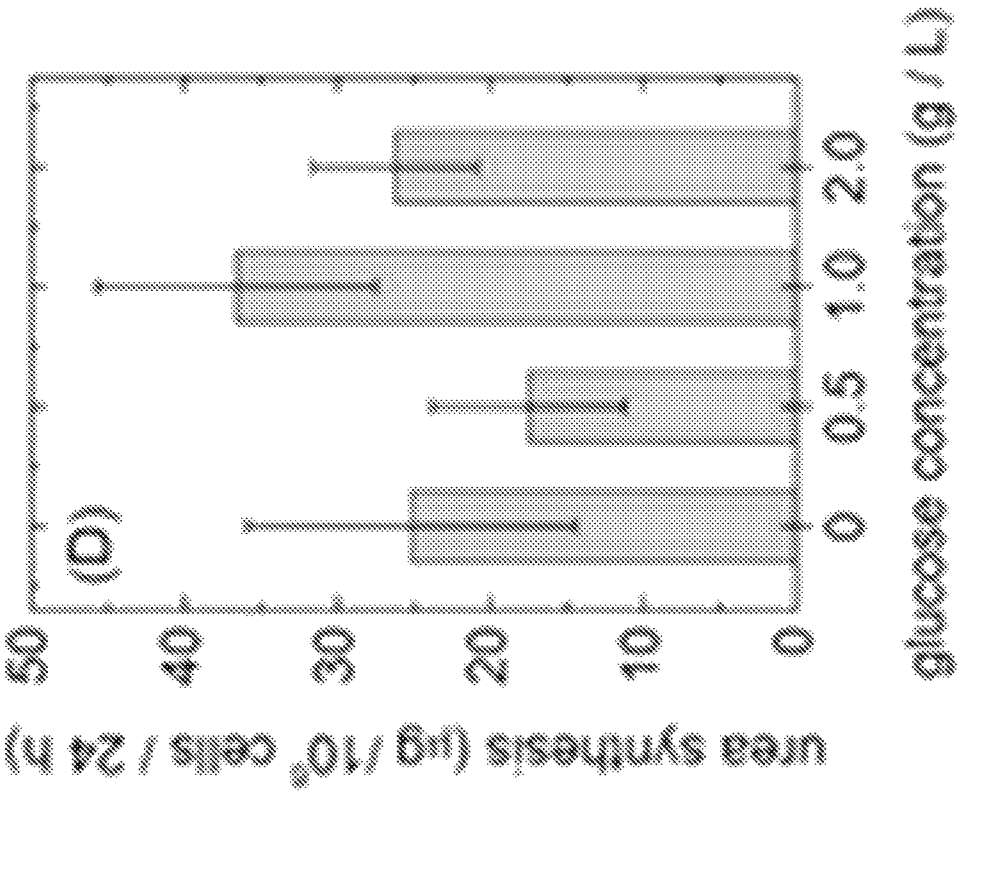
Figure 11C:
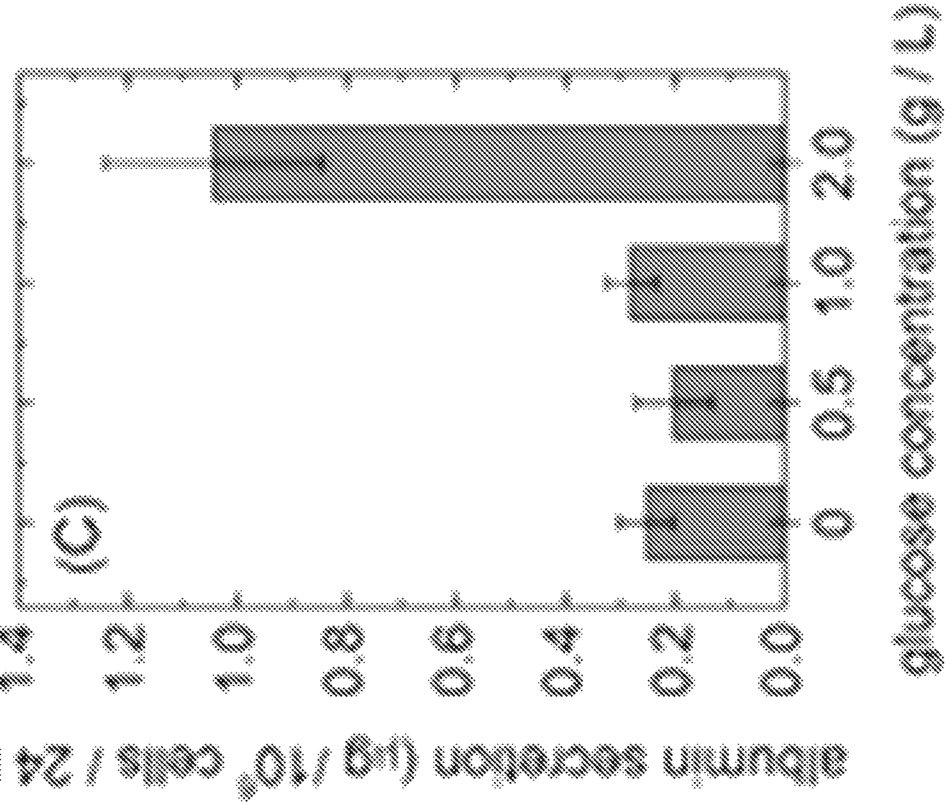

In addition to analyzing tissue response to different flow rates, tissue response to reduction in glucose was also analyzed. Media exchange rates were chosen to be 0.25 mL/24 h and William's E media was formulated to have glucose concentrations of 0 g/L, 0.5 g/L, 1.0 g/L, and 2.0 g/L. These compositions were achieved by mixing full William's E media (2.0 g/L glucose) with glucose-free William's E media at different ratios. Using the same procedures described above, albumin secretion was reduced at all lowered glucose levels, while sharply rising between 1.0 g/L and 2.0 g/L. Urea synthesis showed no systematic dependence on glucose levels, though the maximum urea synthesis rate occurred using media having 1.0 g/L glucose (FIGS. 11C-11D).

Figure 12:
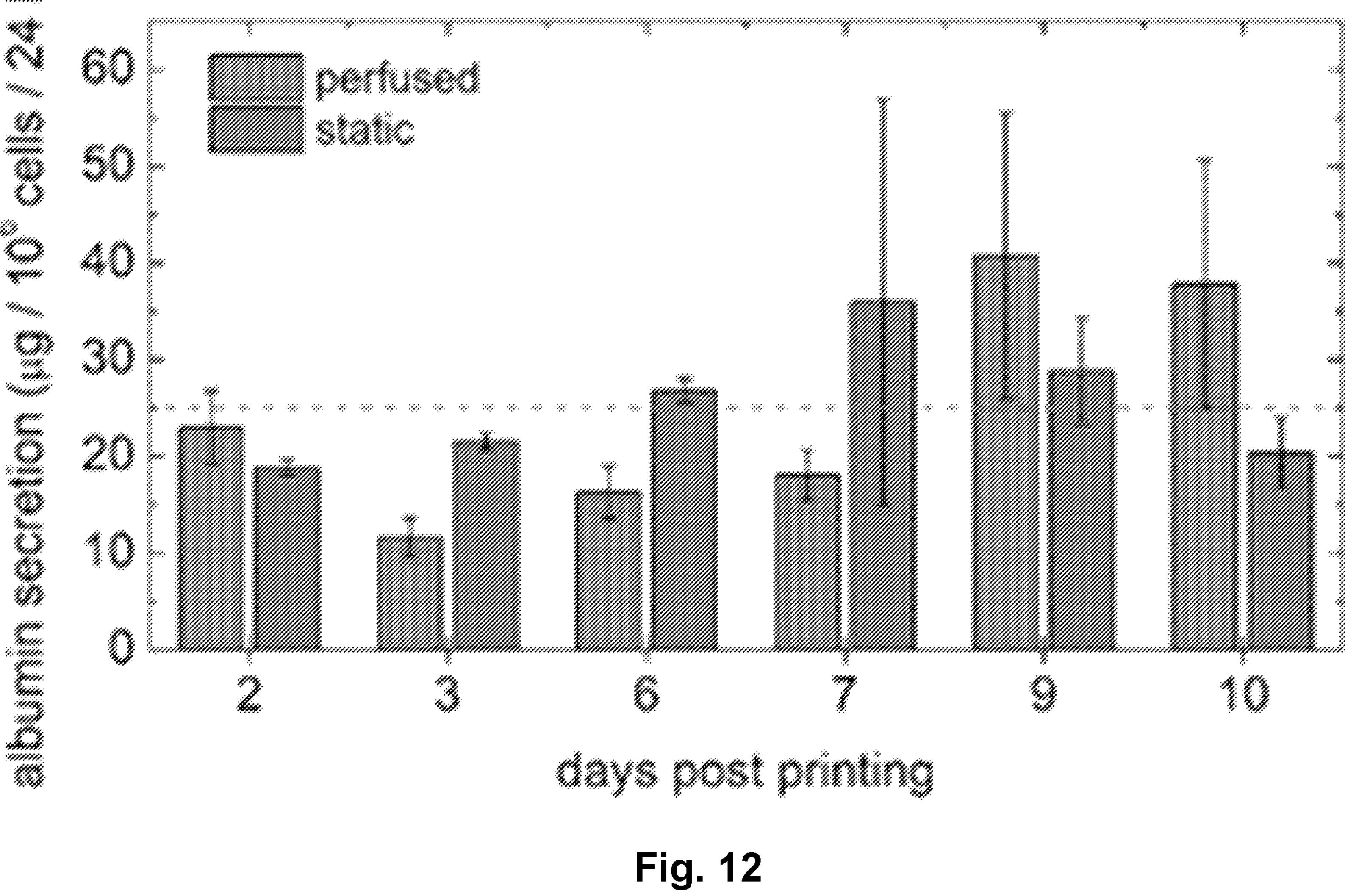
FIG. 12 provides a graph comparing perfused tissues to tissues in static culture. These measurements indicated that perfused tissues exhibited higher albumin secretion rates at later time-points than tissues in static culture. The dashed line is the target albumin secretion rate for this project.

The 96 well tests were performed using intermittent, rapid exchanges of media. To test tissue response to continuous flow, experiments on 3D printed primary hepatocytes (ThermoFisher) were performed in 1 mg/mL collagen-1 using the 12-well system fit with 34-gauge needles as flow restrictors into each well. Slow exchange of 2 mL of media per day was possibly with this setup. Albumin concentrations were measured using the previously described methods and the tissues were harvested at 6 time-points over the course of 10 days. To convert measured albumin concentrations and cell-counts to secretion rates, a computational model like that described above was developed for the 12 well system, which included the known flow profile. Additionally, parallel experiments were performed in static culture with the same total sample volumes and media exchange rates. In the static case, molecular transport from the tissue to the media head was modeled as purely diffusive with no convection. Together, these results showed that perfused tissues exhibited higher albumin secretion rates at later time-points than did tissues in static culture (FIG. 12). Notably, both tissues exceeded the target 25 μg/106 cells/24 h rate.

ASPECTS OF THE DISCLOSURE

The present disclosure will be better understood upon reading the following numbered aspects, which should not be confused with the claims. Any of the numbered aspects below can, in some instances, be combined with aspects described elsewhere in this disclosure and such combinations are intended to form part of the disclosure.

Aspect 1. A perfusion system for a well plate, comprising a chamber insert and a reservoir lid. When coupled with a well plate, the chamber insert inserts into wells of the well plate and the reservoir lid forms an intimate fit on top of the well plate. The chamber insert comprises a plurality of well inserts, wherein each well insert has a media supply compartment and a media collection compartment in fluid communication with one another and wherein a bottom of the well insert is open. The reservoir lid comprises a plurality of media supply wells and a plurality of media collection ports. When the perfusion system is assembled, each of the media supply wells is in fluid communication with a corresponding one of the plurality of media supply compartments and each the media collection port is in fluid communication with a corresponding media collection compartment.

Aspect 2. The perfusion system of aspect 1, wherein fluid inserted into the media supply well flows through the media supply compartment into the well by gravity-driven flow.

Aspect 3. The perfusion system of aspects 1 or 2, further comprising a 3D capillary network inserted in the media collection compartment.

Aspect 4. The perfusion system of aspect 3, wherein fluid flowed into the well rises through a capillary in the media collection compartment and is then drawn by capillary forces through the 3D capillary network.

Aspect 5. The perfusion system of aspects 3 or 4, wherein the 3D capillary network is formed by open cell foam, polystyrene, or polyacrylamide beads.

Aspect 6. The perfusion system of aspects 3, 4, or 5, wherein the 3D capillary network is post-shaped and formed from open cell foam or polystyrene.

Aspect 7. The perfusion system of any of the preceding aspects, further comprising press-fit mounts in an underside of the reservoir lid, wherein the press-fit mounts accept a needle to draw fluid from the media collection ports.

Aspect 8. The perfusion system of any of the preceding aspects, further comprising a well plate and well plate lid.

Aspect 9. The perfusion system of any of the preceding aspects, wherein the well plate is a 96-well plate.

Aspect 10. The perfusion system of any of the preceding aspects, wherein the well plate is a 12-well plate.

Aspect 11. The perfusion system of any of the preceding aspects, wherein the reservoir lid has a top configured to mate with a bottom of a lid of the well plate.

Aspect 12. The perfusion system of any of the preceding aspects, wherein the fluid is a liquid culture medium and wherein a plurality of cells and a 3D cell culture medium are disposed in the wells of the well plate.

Aspect 13. The perfusion system of any of any of the preceding aspects, wherein the chamber insert is formed from acetal homopolymer or polystyrene.

Aspect 14. The perfusion system of any of the preceding aspects, wherein the plurality of well inserts are connected to form a strip, and wherein a number of well inserts corresponds to a number of wells in a row of wells in the well plate.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A perfusion system for a well plate, comprising: a chamber insert and a reservoir lid; wherein when coupled with a well plate, the chamber insert inserts into wells of the well plate and the reservoir lid forms an intimate fit on top of the well plate; wherein the chamber insert comprises a plurality of well inserts, wherein each well insert has a media supply compartment and a media collection compartment in fluid communication with one another and wherein a bottom of the well insert is open; wherein the reservoir lid comprises a plurality of media supply wells and a plurality of media collection ports; and wherein when the perfusion system is assembled, each of the media supply wells is in fluid communication with a corresponding one of the plurality of media supply compartments and each of the media collection ports is in fluid communication with a corresponding media collection compartment.

2. The perfusion system of claim 1, wherein fluid inserted into the media supply well flows through the media supply compartment into the well by gravity-driven flow.

3. The perfusion system of claim 1, further comprising a 3D capillary network inserted in the media collection compartment.

4. The perfusion system of claim 3, wherein fluid flowed into the well rises through a capillary in the media collection compartment and is then drawn by capillary forces through the 3D capillary network.

5. The perfusion system of claim 3, wherein the 3D capillary network is formed by open cell foam, polystyrene, or polyacrylamide beads.

6. The perfusion system of claim 5, wherein the 3D capillary network is post-shaped and formed from open cell foam or polystyrene.

7. The perfusion system of claim 1, further comprising press-fit mounts in an underside of the reservoir lid, wherein the press-fit mounts accept a needle to draw fluid from the media collection ports.

8. The perfusion system of claim 1, further comprising a well plate and well plate lid.

9. The perfusion system of claim 1, wherein the well plate is a 96-well plate.

10. The perfusion system of claim 1, wherein the well plate is a 12-well plate.

11. The perfusion system of claim 1, wherein the reservoir lid has a top configured to mate with a bottom of a lid of the well plate.

12. The perfusion system of claim 1, wherein the fluid is a liquid culture medium and wherein a plurality of cells and a 3D cell culture medium are disposed in the wells of the well plate.

13. The perfusion system of claim 1, wherein the chamber insert is formed from acetal homopolymer or polystyrene.

14. The perfusion system of claim 1, wherein the plurality of well inserts are connected to form a strip, and wherein a number of well inserts corresponds to a number of wells in a row of wells in the well plate.

* * * * *